United States Patent
Fujita et al.

(10) Patent No.: US 6,703,350 B2
(45) Date of Patent: Mar. 9, 2004

(54) AGRICULTURAL CHEMICALS COMPOSITION, PREPARATION THEREOF AND THE METHOD FOR SCATTERING THE SAME

(75) Inventors: Shigeki Fujita, Iwata (JP); Tohru Takayanagi, Morioka (JP); Susumu Kato, Shizuoka (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/987,969

(22) Filed: Nov. 16, 2001

(65) Prior Publication Data

US 2002/0098984 A1 Jul. 25, 2002

(30) Foreign Application Priority Data

Nov. 21, 2000 (JP) .......................... 2000-353887

(51) Int. Cl.$^7$ .......................... A01N 25/08; A01N 25/26
(52) U.S. Cl. ...................... 504/367; 514/949; 514/950; 514/951
(58) Field of Search .................... 504/367; 514/949, 514/950, 951

(56) References Cited

U.S. PATENT DOCUMENTS

| | | | | |
|---|---|---|---|---|
| 4,110,466 A | * | 8/1978 | Inoue et al. | 424/274 |
| 5,201,936 A | * | 4/1993 | Bertram et al. | 504/289 |
| 5,589,256 A | * | 12/1996 | Hansen et al. | 428/283 |
| 5,679,364 A | | 10/1997 | Levy | |
| 5,698,210 A | | 12/1997 | Levy | |
| 5,833,733 A | * | 11/1998 | Wada et al. | 71/27 |
| 5,846,553 A | | 12/1998 | Levy | 424/409 |
| 5,858,384 A | | 1/1999 | Levy | 424/405 |
| 5,858,386 A | | 1/1999 | Levy | 424/409 |
| 5,885,602 A | | 3/1999 | Levy | |
| 5,885,605 A | | 3/1999 | Levy | 424/405 |
| 5,902,596 A | | 5/1999 | Levy | 424/405 |
| 5,939,086 A | | 8/1999 | Levy | |
| 6,001,382 A | | 12/1999 | Levy | 424/405 |
| 6,335,027 B1 | | 1/2002 | Levy | 424/405 |
| 6,337,078 B1 | | 1/2002 | Levy | 424/406 |
| 6,346,262 B1 | | 2/2002 | Levy | 424/405 |
| 6,350,461 B1 | | 2/2002 | Levy | 424/405 |
| 6,387,386 B1 | | 5/2002 | Levy | 424/405 |
| 6,391,328 B1 | | 5/2002 | Levy | 424/405 |

FOREIGN PATENT DOCUMENTS

| | | |
|---|---|---|
| AU | 689716 | 11/1996 |
| AU | 691758 | 2/1997 |

* cited by examiner

*Primary Examiner*—S. Mark Clardy
(74) *Attorney, Agent, or Firm*—Oblon, Spivak, McClelland, Maier & Neustadt, P.C.

(57) ABSTRACT

In an agricultural chemicals composition which is scattered by being thrown directly into a submerged paddy field, it is an object to provide a composition having an excellent spreadability without stagnation of an agrochemically active ingredient at the point of treatment (application), and in particular to provide a labor-saving formulation for scattering (application) which contains a liquid agrochemically active ingredient at room temperature, and to provide an agricultural chemicals composition containing a liquid agrochemically active ingredient at room temperature in high concentrations, which have been difficult to be realized. The agricultural chemicals composition prepared by letting a granular nucleus coated with a water-soluble polymer or water-swellable substance hold agrochemically active ingredients and, if necessary, surfactants, and a method of scattering (applying) a granular agricultural chemicals formulation comprising the step of throwing the agricultural composition directly into a submerged paddy field at a rate of 20 g to 2,000 g thereof per 10 are of the paddy field, or packing 10 g to 100 g of the agricultural chemicals composition per bag made of a water-soluble film and throwing directly into a paddy field at a rate of 2 to 20 bags per 10 are.

21 Claims, 1 Drawing Sheet

AGRICULTURAL CHEMICALS COMPOSITION, PREPARATION THEREOF AND THE METHOD FOR SCATTERING THE SAME

FIELD OF THE INVENTION

The present invention relates to an agricultural chemicals composition to scatter (apply) directly on the water surface of a rice paddy field, water for irrigation, a pond and the like, the preparation thereof and the method for scattering (applying) the same.

DESCRIPTION OF RELATED ART

At present, as a major agricultural chemicals formulation, a granulated type, a powder type, an emulsifiable type, a wettable type, a suspension type, a granulated hydrate type and so on are known. In recent years, saving labor for scattering (applying) agricultural chemicals and cutting down of agricultural chemicals have become important and improvement of the formulation form of the agricultural chemicals is required.

Under these circumstances, recently, labor-saving formulations which can be scattered (applied) only by throwing the agricultural chemicals from a path between rice paddy fields without entering into the rice paddy have been studied. Such a formulation is premised on being scattered in a rice paddy field unevenly, and therefore it has been demanded to develop a formulation whose agrochemically active ingredients float and spread on the water surface without sedimentation of the agricultural chemicals formulation at the treatment (application) point to obtain a desirable spreadability of the components.

Various studies have been made for such a demand, but actually no agricultural chemicals formulation has been obtained, which is perfectly satisfactory for agrochemically active ingredients having various properties. For instance, a method to pack emulsion containing an agrochemical insecticide ingredient in a water-soluble film and to throw it into a submerged paddy field is disclosed (Japanese Patent Publication No. Sho 42-5240). However, the technology disclosed here has a disadvantage that a large quantity of the agricultural chemicals ingredients remain in the soil at the point of throwing after the treatment.

Various technologies are known, for instance, a formulation in which agrochemically active ingredients are impregnated into a foamed plastic material having particle sizes of 0.1 mm to 10 mm and packed with a water-soluble film (Japanese Patent Laid-open No. Sho 53-99327); an agricultural chemicals formulation for throwing into a paddy field in which water-floatable solid agricultural chemicals containing an agrochemically active ingredient, a water-floatable granular nucleus chosen from calcined vermiculite, foamed pearlite, foamed shirasu, and cork, a specific surfactant (acetylene alcohol) are packed with a water-soluble film (Japanese Patent Laid-open No. Hei 6-336403); and a formulation in which agrochemically active ingredients of agricultural chemicals are coated on and carried by a granular nucleus such as pumice or calcined pearlite having apparent specific gravity of less than 1 and particle sizes of 0.3 mm to 1.4 mm and packed with a water-soluble film (Japanese Patent Laid-open No. Hei 9-183701). However, there may arise a problem in spreadability of the components because a portion of the formulation settles down on the bottom of the water at the point of the treatment (application), and a disadvantage that since much quantity of the agrochemically active ingredient still remains on the granular nucleus made of a foamed plastic material, pumice, calcined pearlite, or the like after the treatment (application), the desired effect of the agricultural chemicals can not be exhibited but, on the contrary, phytotoxicity may arise from bringing the agricultural chemicals gathered together by the wind.

Furthermore, as for a granular water-floatable insecticide in which an insecticide is coated on atactic polypropylene granules using a binder (Japanese Patent Publication No. Sho 45-9560), and a floatable granular formulation in which an insecticide component is firmly fixed on calcined pearlite with polybutene (Japanese Patent Publication No. Sho 47-1240), since much quantity of the agrochemically active ingredients remain on the granular nucleus, as similarly as above, the result is not only that the desired effect of the agricultural chemicals can not be exhibited but phytotoxicity may arise because the agricultural chemicals are gathered together by the wind.

In addition, in the conventional art, it has been difficult to obtain a labor-saving scattering (application) type formulation containing agrochemically active ingredients which are liquid at room temperature.

SUMMARY OF THE INVENTION

In an agricultural chemicals formulation to be thrown directly into a submerged rice paddy field to be scattered, an object of the present invention is to provide a composition having an excellent spreadability without stagnation of agrochemically active ingredients at the point of treatment, and in particular, to realize a labor-saving scattering (application) type formulation containing agrochemically active ingredients which are in a liquid state at room temperature, which has been hitherto difficult to realize. Further, it is an object to make the formulation contain a high concentration of the agrochemically active ingredients in a liquid state at room temperature.

As a result of assiduous study to achieve the above-described objects, the present inventors have found that a formulation using a granular nucleus coated with a water-soluble polymer or a water-swellable substance, to hold an agrochemically active ingredient is possible to be scattered (applied) on a rice paddy field only by being thrown from a path between the paddy fields without entering into the paddy fields and, in addition, it has excellent spreadability without sedimentation of the formulation at the point of the treatment (application). Based upon this finding, the inventors have accomplished the present invention.

That is, the present invention is to provide an agricultural chemicals composition, which is prepared by letting a granular nucleus coated with a water-soluble polymer or a water-swellable substance hold an agrochemically active ingredient.

In addition, the present invention is to provide a method of producing the above-described agricultural chemicals composition comprising the step of letting an impregnation-treated granular nucleus which is obtained by impregnating the granular nucleus with solution of a water-soluble polymer or disperse liquid of a water-swellable substance and then removing the solvent thereof by evaporation, hold agrochemically active ingredients and surfactants.

Furthermore, the present invention is to provide a method of scattering (applying) the above-described agricultural chemicals composition, comprising the step of throwing it directly in a submerged paddy field at a rate of 20 g to 2,000 g of the agricultural chemicals composition or 2 to 20 bags of the agricultural chemicals composition packed with a water-soluble film per 10 are of the paddy field.

DETAILED DESCRIPTION OF THE PREFERRED EMBODIMENTS

Figure 1:
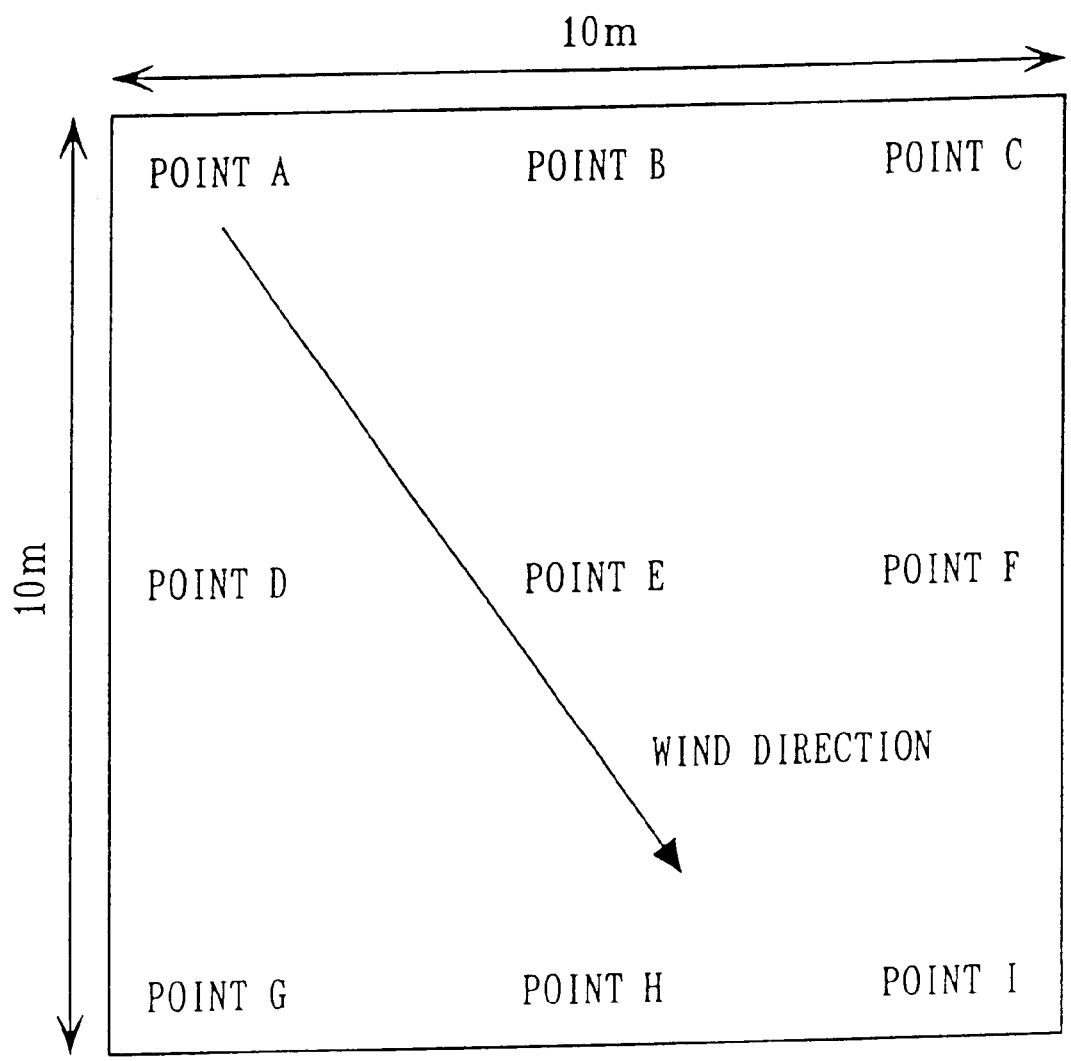
FIG. 1 shows a rice paddy field having an area of 10 m by 10 m, used in the Test Example 2. The point E is a point of treatment (application) with an agricultural chemicals composition for a rice paddy field.

An agricultural chemicals composition of the present invention includes a granular composition composed of agrochemically active ingredients held by a granular nucleus coated with a water-soluble polymer or a water-swellable substance, and an agricultural chemicals formulation in which the above-described granular composition is further packed in a water-soluble film bag.

On the preparation of the agricultural chemicals composition of the present invention, it is necessary first to coat the granular nucleus in advance with a water-soluble polymer or a water-swellable substance. As a method for this purpose, the following method can be cited. That is, first, a water-soluble polymer solution or disperse liquid of a water-swellable substance which will be described later is prepared, with which the above-mentioned granular nucleus is then impregnated, and thereafter the solvent thereof is evaporated out.

The granular nucleus here is a solid base material which can hold the agrochemically active ingredient, and as a granular nucleus which can be used in the present invention, a water-insoluble solid carrier can be cited. For instance, mineral matter such as pumiceous sand, venniculite, pearlite, and a piece of vegetable matter such as a rice hull, sugar cane, rice straw, wheat straw, coconut, banana, bamboo, reed, kenaf and wood can be cited. Among them, a piece of the vegetable matter is more preferable, because it is undergone time-varying corrosive decomposition after the treatment (application). Especially, kenaf of the genus Confederate rose in Hollyhock family (Hibiscus cannabinus Linn./Hibiscus Sabdariffa Linn.) is suitable.

A granular nucleus having the shorter diameter of 0.1 mm to 10 mm and bulk specific gravity of 1 or less is preferable for these granular nuclei. The ratio of the shorter diameter to the longer diameter is between 1 to 20, in general. These nuclei have some buoyancy and float on the water surface when they are alone. However, when they are processed to hold an agrochemically active ingredient having the specific gravity of 1 or more, the buoyancy is lowered and most of or a part of the granular nuclei settle down on the bottom of the water. The present invention aims to improve the buoyancy of the nucleus itself so that the nucleus becomes hard to settle down on the bottom of the water when it holds an agrochemically active ingredient.

As a water-soluble polymer used to coat the above-described granular nucleus, any substance which is preferably a solid at room temperature and not soluble in the above-described liquid agrochemically active ingredient at room temperature is acceptable. Especially, a substance having the viscosity in 1% aqueous solution of 10 mPa·s or more is preferable, and the solution having the viscosity of 100 mPa·s or more is more preferable. Further, the solution having the viscosity of 500 mPa·s or more is much more preferable. The viscosity of the aqueous solution can be measured with, for instance, a rotational viscometer and the like.

As concrete examples of the water-soluble polymer, sodium polyacrylate, dextrin, polyvinyl alcohol, carboxymethyl cellulose, xanthan gum, gum arabic, polyvinyl pyrolidone having a molecular weight of 5000 or more, and polyalkylene glycol having a molecular weight of 100,000 or more can be cited but it is not limited to these substances. These water-soluble polymers can be used alone or as a mixture of two kinds or more.

A water-swellable substance which is another ingredient used for coating the above-described granular nucleus is preferably a solid at room temperature which does not dissolve in the above-described liquid agrochemically active ingredient at room temperature, and more concretely, bentonite is preferable. Bentonite belongs to a group of typical minerals which constitute clay, and designates montmorillonite group minerals and a mineral group having the montmorillonite group minerals as a major constituent. It is comprised of phyllosilicate mineral having a three-layered structure and a part thereof is sometimes substituted by a metal such as sodium, calcium, magnesium and the like. Particularly, bentonite which contains sodium is preferable in the present invention.

As a solvent to prepare the above-described water-soluble polymer solution or disperse liquid of the water-swellable substance described above, there is no limitation especially provided that it can be removed by evaporation after the granular nucleus is coated with these ingredients. However, water is preferable as the solvent from a safety and hygienic point of view at the time of removing the solvent by evaporation.

The concentration of the water-soluble polymer or the swellable substance in the solution or in the disperse liquid differs depending on the sort of the water-soluble polymer or the water-swellable substance, but since it is preferable to be in the range where the handling thereof is suitable, the viscosity of the above-described solution or disperse liquid is generally adjusted to be 3000 mPa·s or less. As the concentration of the water-soluble polymer solution, it is generally in the range of 0.1% to 10%, and as the concentration of the disperse liquid of the water-swellable substance, it is generally in the range of 1% to 20%. The amount of the water-soluble polymer solution or the disperse liquid of the water-swellable substance for impregnating the granular nucleus differs depending on the sort of the granular nucleus, but for convenience of removing operation of the solvent, it is preferable to adjust the amount in such that the granular nucleus can flow when impregnated with the solution or the disperse liquid, which is generally 10 parts by weight to 600 parts by weight for 100 parts by weight of the granular nucleus. As for a method to remove the solvent from the granular nucleus impregnated with the water-soluble polymer solution by evaporation, for instance, a method of evaporating it by hot air, a method to heat it under reduced pressure and the like can be cited, but it is not particularly limited to a specific method.

In thus obtained granular nucleus coated with the water-soluble polymer or water-swellable substance (hereinafter referred to as "a coated granular nucleus"), the above-described water-soluble polymer or water-swellable substance is contained in a rate of 0.01 parts by weight to 50 parts by weight, preferably 0.2 parts by weight to 20 parts by weight for 100 parts by weight of the granular nucleus.

It is desirable that the coated granular nucleus obtained thus is contained in the final agricultural chemicals composition of the present invention at a rate of generally 5 parts by weight to 60 parts by weight, more preferably from 10 parts by weight to 50 parts by weight for 100 parts by weight of the final agricultural chemicals composition.

In the agricultural chemicals composition of the present invention, the agrochemically active ingredient held by the above-described coated granular nucleus is preferably in a liquid state, but even when it is a solid, it is acceptable if it can be made liquid matter by dissolving or dispersing in a solvent, as well as it is liquid as itself. Therefore, the agrochemically active ingredient is not limited in particular, and both solid chemicals and liquid chemicals, regardless of being readily soluble or slightly soluble in water, can be used so far as they can be generally used as agricultural chemicals. As such an agrochemically active ingredient, for instance, herbicide, fungicide, insecticide, PGR (plant growth regulator), and the like can be cited. Especially, substances advantageously used for a paddy treatment on the water surface are preferable.

Among agrochemically active ingredients of the agricultural chemicals used in the present invention, the examples which can be cited in a liquid state at room temperature are a herbicide such as 2-methyl-4-chlorophenoxy-thioacetic acid-s-ethyl (phenothiol), S-(4-chlorbenzyl) N,N-diethylthiocarbamate (benthiocarb), S-benzyl=1,2-dimethlpropyl (ethyl) thiocarbamate (esprocarb), S-ethylhexahydro-1H-azepin-1-carbothioate (molinate), 2-chloro-2',6'-diethyl-N-(butoxymethyl) acetanilide (butachlor), 2-chloro-2',6'-diethyl-N-(2-propoxyethyl) acetanilide (pretilachlor), and ethyl 4-(4-chloro-o-tryloxy) butylate (MCPB-ethyl), a fungicide such as O,O-diisopropyl-S-benzylthiophosphate (IBP) and so on, insecticide such as O,O-dimethyl-O-(3-methyl-4-nitrophenyl) thiophosphate (MEP), 2-isopropyl-4-methylpyrimidyl-6-diethylthiophosphate (diazinon), dimethyldicarbethoxyethyldithiophosphate (malathion), O,O-dipropyl-O-4-methylthiophenylphosphate (propaphos), 2,3-dihydro-2,2-dimethyl-7-benzo[b]flanyl=N-dibutylaminothio-N-methylcarbamate (carbosulfan), ethyl=n-[2,3-dihydro-2,2-dimethylbenzoflan-7-yloxycarbonyl (methyl) aminothio]-N-isopropyl-.beta.-alanynate (benfuracarb), (RS)-.alpha.-cyano-3-phenoxybenzyl=(RS)-2,2-dichloro-1-(4-ethoxyphenyl)cyclopropane carboxylate (cycloprothrin) can be cited for each kind of chemicals.

As an example of a solid agrochemical active ingredient at room temperature among the agricultural chemicals ingredients used in the present invention, a herbicide such as 2,4,6,-trichlorphenyl-4'-nitrophenylether (CNP),.alpha.-(2-naphthoxy) propionanilide (naproanilide), 5-(2,4-dichlorophenoxy)-2-nitrobenzoate methyl (bifenox), S-1-methyl-1-phenylethyl=piperidine-1-carbothioate (dimepypelate), O-3-tert-butylphenyl=6-methoxy-2-pyridyl (methyl) thiocarbamate (pyributicarb), (RS)-2-bromo-N-(.alpha.,.alpha.-dimethylbenzyl)-3,3-dimethylbutylamide (bromobuthyde), 2-benzothiazol-2-yloxy-N-methylacetanilide (mefenacet), 1-(.alpha.,.alpha.-dimethylbenzyl)-3-(paratryl) urea (dimron), methyl=.alpha.-(4,6-dimethoxypyrimidine-2-ylcarbamoylsulfamoyl)-O-toluate (bensulfuron-methyl), 1-(2-cloroimidazo[1,2-a]pyridine-3-ylsulfonyl)-3-(4,6-dimethoxypyrimidine-2-yl) urea (imazosulfion), ethyl=5-(4,6-dimethoxypyrimidine-2-ylcarbamoylsulfamoyl)-1-methylpyrasol-4-carboxylate (pyrazosulfuron-ethyl), 2-methylthio-4,6-bis(ethylamino)-s-triazine (simetryne), 2-methylthio-4,6-bis (isopropylamino)-s-triazine (prometryn), 2-methylthio-4-ethylamino-6-(1,2-dimethylpropylamino)-s-triazine (dimethametryn), 2,4-dichlorophenyl-3'-methoxy-4'-nitrophenylether (chiomethoxynil), 5-tert-butyl-3-(2,4-dichoro-5-isopropoxyphenl)-1,3,4-oxadiazorin-2-one (oxadiazon), 4-(2,4-dichlorobenzoyl)-1,3-dimethyl-5-pyrazoryl-p-toluensulfonate (pyrazolate), 2-[4-(2,4-dichlorobenzoyl)-1,3-dimethylpyrazole-5-yloxy]acetophenone (pyrazoxyfen), (RS)-2-(2,4-dichloro-m-tolyloxy) propionanilide (clomeprop), 2-[4-[2,4-dichloro-m-toluoyl) -1,3-dimethylpyrazole-5-yloxy]-4'-methylacetophenon (benzofenap), S,S'-dimethyl=2-difluoromethyl-4-isobutyl-6-trifluoromethylpyridine-3,5-dicarbothioate (dithiopyl), 2-chloro-N-(3-methoxy-2-thenyl)-2',6'-dimethylacetanilide (thenyichior), n-butyl-(R)-2-[4-(2-fluoro-4-cyanophenoxy) phenoxy]propionate (sypharophopbutyl), 3-[1-(3,5-dichlorphenyl)-1-methylethyl]-2,3-dihydro-6-methyl-5-phenyl-4H-1,3-oxazine-4-one (oxazichlomefone), 3-(4-chloro-5-cyclopentyloxy-2-fluorophenyl)-5-isopropyridene-1,3-oxazolidine-2,4-dione (pentoxazone), 1-(diethylcarbamoyl)-3-(2,4,6-trimethylphenylsulfonyl)-1,2,4-triazole (cafenstrole), N-{[(4,6-dimethoxypyrimidine-2-yl) aminocarbonyl]}-1-methyl-4-(2-methyl -2H-tetrazole-5-yl) (azimsulfuron), methyl 2-[(4,6-dimethoxypyrimidine-2-yl) oxy]-6-[(E)-1-(methoxyimino) ethyl]benzoate (pyriminobac-methyl), 4-(2-chloro-phenyl)-5-oxo-4,5-dihydro-tetrazole-1-carboxylic acid cyclohexyl-ethyl-amide (fentrazamide) and so on, a fungicide such as 3'-isopropoxy-2-methylbenzanilide (mepronil), .alpha.,.alpha.,.alpha.-trifluoro-3'-isopropoxy-O-toluanilide (flutolanil), 3 ,4,5,6-tetrachloro-N-(2,3-dichlorophenyl) phthalamid acid (tecloftalam), 1-(4-chlorobenzyl)-1-cyclopentyl-3-pheny urea (pencycuron), 6-(3,5-dichloro-4-methylphenyl)-3 (2H)-pyridazinone (diclomezin), methyl=N-(2-methoxyacetyl)-N-(2,6-xylyl)-DL-alaninate (metalaxyl), (E)-4-chloro-.alpha.,.alpha.,.alpha.-trifluoro-N-(1-imidazole-1-yl-2-propoxyethylidene)-o-tol uidine (triflumizole), [5-amino-2-methyl-6-(2,3,4,5,6-pentahydroxycyclohexycyloxy) tetrahydropylan-3-yl] amino-.alpha.-iminoacetic acid (kasugamycin), baridamicine, 3-aryloxy-1,2-benzoisothiazole-1,1-dioxyd (probenazole), diisopropyl-1,3-dithiolan-2-ylidene-malonate (isoprothiolane), 5-methyl-1,2,4-triazoro [3,4-b] benzothiazole (tricyclazole), 1,2,5,6-tetrahydropylolo[3,2,1-ij]chinoline-4-one (pyroquilon), 5-ethyl-5,8-dihydro-8-oxo [1,3]dioxolo[4,5-g]chinoline-7-carboxylic acid (oxolinic acid), (Z)-2'-methylacetophenone=4,6-dimethylpyrimidin-2-ylhydrazone 4,5,6,7-tetrachlorophthalide (ferimzone), 3-(3,5-dichlorophenyl)-N-isopropyl-2,4-dioxoimidazolidine-1-carboxyamide (iprodione), and so on, insecticide such as 1-naphthyl-N-methylcarbamate (NAC), O,O-diethyl-O-(3-oxo-2-phenyl-2H-pyridadine-6-yl) phosphorothioate (pyridaphenthion), O,O-dimethyl-O-3,5,6-trichoro-2-pyridylphosphorothioate (chlorpyrifos-methyl), O,O-dimethyl-S-(N-methylcarbamoylmethyl) dithiophosphate (dimethoate), O,S-dimethyl-N-acetylphosphoroamidethioate (acephate), ethylparanitrophenylthiono bennzene phosphonate (EPN), 2-secondary-butylphenyl-N-methyylcarbamate (BPMC), 2-(4-ethoxyphenyl)-2-methylpropyl=3-phenoxybenzyl=ether (etofenprox), 1,3-bis (carbamoylthio)-2-(N,N-dimethylamino) propane hydrochloride (cartap), 5-dimethylamino-1,2,3-trithian oxalate (thiocyclam), S,S'-2-dimethylamino trimethylene=di (benzenthiosulfonate) (bensultap), 2-tert-butylimino-3-isopropyl-5-phenyl-1,3,5,6 tetrahydro-2H-1,3,5-thiadiazine-4-one (buprofezin), and so on, and a PGR (plant growth regulator) such as 4'-chloro-2'-(.alpha.-hydroxybenzyl) isonicotinanilide (inabenfide), (2RS, 3RS)-1-(4-chlorophenyl)-4,4-dimethyl-2-(1H-1,2,4-triazole-1-yl) pentane-3-ol (paclobutrazol), (E)-(S)-1-(4-chlorophenyl)-4,4-dimethyl-2-(1H-1,2,4-triazole-1-yl) penta-1-ene-3-ol (uniconazole) can be cited. However, the agrochemically active ingredients used in the present invention are not limited to these chemicals described above.

In the present invention, when the agrochemically active ingredient of the agricultural chemicals is liquid at room temperature, it can be used as it is, but when it is a solid at room temperature, it is desirable to use after converting it into a liquid state by dissolving it or dispersing it into a solvent. As a solvent capable of being used to dissolve or disperse a solid agrochemically active ingredient of the agricultural chemicals, any solvent generally used for an agricultural chemicals formulation can be used as far as it does not react with the agrochemically active ingredient, and does not dissolve a water-soluble film. As a concrete example of the solvent, an organic solvent such as dioctylphthalate, methylnaphthalene, alkyl pyrrolidone, phenylxyrylethane, glycerine, alkylene glycol, xylene, kerosine, machine oil, methane series hydrocarbon, fatty acid ester, polybasic acid, coconut oil, soybean oil, rapeseed oil, and silicone oil, and furthermore, above-described agrochemically active ingredients in a liquid state at room temperature can be cited. Especially, the solvent having a specific gravity of 1 or less is preferable. As the compounding amount of these solvents, a range from 10 parts by weight to 200 parts by weight for 100 parts of the solid agrochemically active ingredients of the agricultural chemicals is preferable in general. These solvents can be used for an additive to an agrochemically active ingredient of the agricultural chemicals in a liquid state at room temperature, as necessary.

The agrochemically active ingredient of the agricultural chemicals described above can be used alone or as a mixture of two kinds or more. As the total amount of the agrochemically active ingredients blended in the agricultural chemicals, 0.1 parts by weight to 70 parts by weight for 100 parts by weight of the agricultural chemicals composition is generally preferable.

In the agricultural chemicals composition of the present invention, in case of necessity, in order to obtain a desirable disperse liquid of the agrochemically active ingredients in water after the composition being thrown into a paddy field, it is preferable to let the coated granular nucleus hold a surfactant therein. As a usable surfactant, surfactants generally used in the agricultural chemicals formulation can be cited. As concrete examples of the surfactants, nonionic surfactant such as polyethylene glycol higher fatty acid ester, polyoxyethylene alkylether, polyoxyethylene alkylarylether, polyoxyethylene arylphenylether, sorbitanmonoalkylate, acetylene alcohol, acetylene diol, and alkylene oxide additives thereof; anionic surfactant such as alkylaryl sulfonate, dialkyl sulfonate, lignin sulfonate, naphthalene sulfonate and its condensate, alkyl sulfate ester, alkyl phosphate ester, alkylarylsulfate ester, alkylaryl phosphate ester, polyoxyethylene alkylether sulfate ester, polyoxyethylene alkylarylether sulfate ester, polyoxyethylene arylphenylether sulfate ester, polycarboxylic acid type polymer surfactant, further a silicone series surfactant, fluorine series surfactant can be cited. These surfactants can be used alone or as a mixture of two kinds or more.

The rate of these surfactants to be used in the formulation is generally from 0.1 parts by weight to 30 parts by weight for 100 parts by weight of the agricultural chemicals composition, preferably from 0.5 parts by weight to 20 parts by weight, more preferably from 2 parts by weight to 10 parts by weight.

In the present invention, in addition to the above-described respective components, substances usually used in an agricultural chemicals formulation such as a filler, active ingredient stabilizer, physical property improvement agent can be used as supplementary additives as necessary, and these additives can be in a solid state or in a liquid state, and can be slightly soluble or readily soluble in water. As these supplementary additives, fine mineral particles such as clay, calcium carbonate, talc, diatomite, and white carbon; organic or inorganic salt such as ammonium sulfate, ammonium bicarbonate, ammonium nitrate, ammonium chloride, potassium chloride, sodium sulfate, magnesium sulfate, sodium citrate, sodium carbonate, sodium hydrogen carbonate; organic acids such as citric acid, and succinic acid; sugars such as cane sugar, lactose, xanthan gum; water-soluble fine powders such as urea; expanded shirasu made of shirasu, inorganic substances such as filite made of calcined alminosilicates, microbaloons which are made by expanding sodium silicate or borax, fly ash, pumice, ceramic hollow body, and so on, phenol microbaloon made by phenol resin, echo-sphere made of epoxy resin, polyurethane foam made from polyurethane, microsphere made of vinylidene chloride and acrylonitrile copolymer and so on can be cited. Thus, a hollow body or dyestuff having 10 $\mu$m to 600 $\mu$m in particle diameter, and having single, or two or more independent foams can be cited, but it is not limited to these substances.

The preparation of the agricultural chemicals composition of the present invention can be carried out according to the ordinary manner except using the coated granular nucleus. For instance, liquid matter is obtained by dissolving or suspending liquid agrochemically active ingredients at room temperature or solid agrochemically active ingredients at room temperature in a solvent, to which surfactants and additives are added and mixed as necessary to obtain the liquid matter or suspended liquid matter. The agricultural chemicals composition of the present invention can be obtained by adding and mixing the coated granular nucleus to the above-described liquid matter or the suspended liquid matter so that these components are held by the granular nucleus. Incidentally, the components to be held by the coated granular nucleus are not always required to be carried simultaneously, but they may be held one by one.

The agricultural chemicals composition of the present invention obtained in this manner may be further packed in a water-soluble film as necessary so as to be an agricultural chemicals formulation.

When the agricultural chemicals formulation described above is produced, a suitable water-soluble film to be used is a film which is dissolved or dispersed rapidly into water. As a film material, polyvinyl alcohol, polyoxy polyalkylene glycol, hydroxypropylcellulose, hydroxypropylmethylcellulose, methylcellulose, sodium carboxymethylcellulose, sodium polyacrylate, alginic acid, gelatine, pulran, soluble starch and further water-soluble paper, water-dispersible paper are cited as examples. However, it is not limited to these specific materials.

The thickness of the water-soluble film used for the packing of the composition is not particularly limited, however it is generally preferable to have the thickness of about 20 $\mu$m to about 100 $\mu$m. It is also acceptable to pack in multiple layers with water-soluble films of the same composition or different composition. In order to restrain formation of an air dome, and to make the dissolution of the water-soluble film better when the treatment is carried out, it is acceptable to make holes of about 0.1 mm to about 1 mm in diameter in the water-soluble film at a rate of 1 to 100 per bag of the agricultural chemicals formulation. Alternatively, a gap to make air pass through may be provided on the heat sealing portion when the heat sealing is carried out as will be described later.

Packing of the agricultural chemicals composition of the present invention into a water-soluble film is carried out according to the ordinary manner. For instance, a water-soluble film sheet is bent to make a bag with a heat sealer and the like, to which the composition prepared as described above is filled in. Then the opening of the bag is sealed with a heat sealer and the like so that the agricultural chemicals composition of the present invention can be obtained. Incidentally, the weight of the agricultural chemicals composition of the present invention is preferably about 10 g to about 200 g per bag.

Scattering (application) of the agricultural chemicals composition of the present invention obtained thus is carried out by directly throwing 20 g to 2,000 g of the agricultural chemicals composition per 10 are of the submerged paddy field from a path between rice paddy fields or from a water inlet. Scattering (application) of the agricultural chemicals formulation of the present invention is carried out by directly throwing 2 bags to 20 bags of the formulation per 10 are. Incidentally, the agricultural chemicals composition or the agricultural chemicals formulation of the present invention can be scattered (applied) not only to a paddy field, but also to water for irrigation, pond and the like in a similar manner.

The agricultural chemicals composition of the present invention is characterized in that the agrochemically active ingredient and the like are held by the granular nucleus coated with a water-soluble polymer or a water-swellable substance (coated granular nucleus). That is, the water-soluble polymer or water-swellable substance which coats the granular nucleus seals air in the granular nucleus to make a closed air chamber so that the buoyancy of the granular nucleus is heightened, thereby making the buoyancy greater without using a large amount of organic solvent or an excess amount of the granular nucleus.

That is, the water-soluble polymer or the water-swellable substance exists to make air chambers by itself from the surface layer of the granular nucleus toward inside in the coated granular nucleus, thereby an agricultural chemicals composition can be obtained, which has a heightened buoyancy and therefore no sedimentation of the formulation on the bottom of water at the point of treatment (application). Thus, the water-soluble polymer or the water-swellable substance is not used only for adhering an agrochemically active ingredient to a granular nucleus as is in the case of the conventional agricultural chemicals formulation.

As described above, since the agricultural chemicals composition of the present invention uses the coated granular nucleus having many air chambers, when the agricultural chemicals composition described above or an agricultural chemicals formulation which utilizes this composition is scattered (applied), it shows excellent spreadability without stagnation of the agrochemically active ingredient at the point of treatment (application), which makes it possible to realize a low volume applying formulation.

Hereinafter, the present invention will be explained in detail with examples and test examples. However, the present invention is not limited to the examples. Incidentally, the word "part" indicates "part by weight" in the following examples.

EXAMPLE 1

A 0.5% aqueous solution of sodium polyacrylate having a molecular weight of 1,000,000 to 2,000,000 (the viscosity of 1% aqueous solution is 2,400 mPa·s) is prepared, and this solution and pumice (shorter diameter: 0.2 mm to 0.5 mm, bulk specific gravity: 0.66) are mixed at a weight ratio of 1/1 so that the pumice is impregnated with the aqueous solution. Then, the mixture obtained thus is undergone fluidized bed drying with a hot wind of 80° C. to remove water, and pumice coated with sodium polyacrylate at a rate of 0.5 parts of sodium polyacrylate to 100 parts of pumice is obtained. An agricultural chemicals composition is obtained by mixing 57.5 parts of thus obtained pumice coated with sodium polyacrylate and 42.5 parts of IBP so that IBP is held by the coated pumice. This agricultural chemicals composition is packed in a water-soluble film bag made of polyvinyl alcohol at a rate of 100 g per bag and the bag is sealed with a heat sealer. Thus, the agricultural chemicals formulation of the present invention is obtained, which is scattered (applied) at a rate of 20 bags per 10 are of a paddy field to be applied.

EXAMPLE 2

A 0.5% aqueous solution of sodium polyacrylate having a molecular weight of 1,000,000 to 2,000,000 (the viscosity of 1% aqueous solution is 2,400 mPa·s) is prepared, and this solution and kenaf piece (shorter diameter: 0.5 mm to 1 mm, bulk specific gravity: 0.06) are mixed at a weight ratio of 6/1 so that the kenaf piece is impregnated with the aqueous solution. Then, the mixture obtained thus is undergone fluidized bed drying with a hot wind of 80° C. to remove water, and the kenaf piece coated with sodium polyacrylate at a rate of 3 parts of sodium polyacrylate to 100 parts of the kenaf piece is obtained. An agricultural chemicals composition is obtained by preparing a liquid first by mixing and dissolving 56 parts of IBP, 2 parts of acetylene alcohol and 2 parts of dialkylsulfosuccinate salt, and then by mixing the whole of this liquid and 40 parts of the kenaf piece coated with sodium polyacrylate described above so that the liquid is carried by the coated kenaf piece. This agricultural chemicals composition is packed in a water-soluble film bag made of polyvinyl alcohol at a rate of 75 g per bag and the bag is sealed with a heat sealer. Thus, the agricultural chemicals formulation of the present invention is obtained, which is scattered (applied) at a rate of 20 bags per 10 are of a paddy field to be applied.

EXAMPLE 3

A 1% aqueous solution of xanthan gum having a molecular weight of about 2,000,000 (the viscosity of 1% aqueous solution is 1,800 mpa·s) is prepared, and this solution and kenaf piece (shorter diameter: 1 mm to 2 mm, bulk specific gravity: 0.06) are mixed at a weight ratio of 2/1 so that the kenaf piece is impregnated with the aqueous solution. Then, the mixture obtained thus is undergone fluidized bed drying with a hot wind of 80° C. to remove water, and a kenaf piece coated with xanthan gum at a rate of 2 parts of xanthan gum to 100 parts of the kenaf piece is obtained. An agricultural chemic is composition is obtained by preparing a liquid first by mixing 43 parts of thiobencarb, 2.1 parts of bensulfuron-methyl, 13.5 parts of mefenacet, 1.2 part of ammonium polyoxyethylene arylphenylether sulfate, 1.5 parts of ammonium polyoxyalkylenealkylether sulfate, and 2.3 parts of dialkylsulfosuccinate salt, and then by mixing the whole of this liquid and 36.4 parts of the kenaf piece coated with xanthan gum described above so that the liquid is carried by the coated kenaf piece. This agricultural chemicals composition is packed in a water-soluble film bag made of polyvinyl alcohol at a rate of 35 g per bag and the bag is sealed with a heat sealer. Thus, the agricultural chemicals formulation of the present invention is obtained, which is scattered (applied) at a rate of 10 bags per 10 are of a paddy field to be applied.

EXAMPLE 4

A 10% bentonite disperse liquid is prepared, and this disperse liquid and kenaf piece (shorter diameter: 1 mm to 2 mm, bulk specific gravity: 0.06) are mixed at a weight ratio of 2/1 so that the kenaf piece is impregnated with the aqueous solution. Then, the mixture obtained thus is undergone fluidized bed drying with a hot wind of 80° C. to remove water, and the kenaf piece coated with bentonite at a rate of 20 parts of bentonite to 100 parts of the kenaf piece is obtained. An agricultural chemicals formulation of the present invention is obtained by preparing a liquid first by mixing 43 parts of thiobencarb, 2.1 parts of bensulfuron-methyl, 13.5 parts of mefenacet, 1.2 parts of ammonium polyoxyethylene arylphenylether sulfate, 1.5 parts of ammonium polyoxyalkylenealkylether sulfate, and 2.3 parts of dialkylsulfosuccinate salt, and then by mixing the whole of this liquid and 36.4 parts of the kenaf piece coated with bentonite described above so that the liquid is carried by the coated kenaf piece. This agricultural chemicals formulation is scattered (applied) at a rate of 350 g per 10 are of a paddy field to be applied.

EXAMPLE 5

A 1% aqueous solution of xanthan gum having a molecular weight of about 2,000,000 (the viscosity of 1% aqueous solution is 1,800 mPa·s) is prepared, and this solution and wood piece (shorter diameter: 0.2 mm to 0.5 mm, bulk specific gravity: 0.23) are mixed at a weight ratio of 1/1 so that the wood piece is impregnated with the aqueous solution. Then, the mixture obtained thus is undergone fluidized bed drying with a hot wind of 80° C. to remove water, and a wood piece coated with xanthan gum at a rate of 1 part of xanthan gum to 100 parts of the wood piece is obtained. An agricultural chemicals composition is obtained by preparing a liquid first by dissolving 3 parts of cyhalofop-butyl into 20 parts of adipic acid diisodecylester, and then by mixing the above solution with 4.2 parts of caffenstrol, 9 parts of daimuron, 1 part of bensulfuron-methyl, 5 parts of polyoxyethylene styrylphenylether sulfate, and 2 parts of acetylene alcohol, and then by mixing the whole of this liquid and 55.8 parts of the wood piece coated with xanthan gum described above so that the liquid is carried by the coated wood piece. The agricultural chemicals composition thus obtained is packed in a water-soluble film bag made of polyvinyl alcohol at a rate of 50 g per bag. The above-described bag is heat-sealed to obtain the agricultural chemicals formulation of the present invention. The agricultural chemicals formulation of this example is scattered at a rate of 10 bags per 10 are.

COMPARISON EXAMPLE 1

An agricultural chemicals composition is obtained by mixing 57.5 parts of pumice (shorter diameter: 0.2 mm to 0.5 mm, bulk specific gravity: 0.66) and 42.5 parts of IBP so that IBP is carried by the pumice. The agricultural chemicals composition obtained thus is packed in a water-soluble film bag made of polyvinyl alcohol at a rate of 100 g of the agricultural chemicals composition per bag. The above-described bag is heat-sealed to obtain an agricultural chemicals formulation.

COMPARISON EXAMPLE 2

An agricultural chemicals composition is obtained by preparing a liquid first by mixing and dissolving 56 parts of IBP, 2 parts of acetylene alcohol and 2 parts of dialkylsulfosuccinate salt, and then by mixing this liquid with 40 parts of kenaf piece (shorter diameter: 0.5 mm to 1 mm, bulk specific gravity: 0.06) so that the liquid is carried by the kenaf piece. The agricultural chemicals composition obtained thus is packed in a water-soluble film bag made of polyvinyl alcohol at a rate of 75 g per bag. The above-described bag is heat-sealed to obtain an agricultural chemicals formulation.

COMPARISON EXAMPLE 3

An agricultural chemicals composition is obtained by preparing a liquid first by mixing 43 parts of thiobencarb, 2.1 parts of bensulfuron-methyl, 13.5 parts of mefenacet, 1.2 parts of ammonium polyoxyethylene arylphenylether sulfate, 1.5 parts of ammonium polyoxyalkylether sulfate, and 2.3 parts of dialkylsulfosuccinate, and then mixing the whole of this liquid and 36.4 parts of kenaf piece (shorter diameter: 1 mm to 2 mm, bulk specific gravity: 0.06) so that the liquid is carried by the kenaf piece. The agricultural chemicals composition thus obtained is packed in a water-soluble film bag made of polyvinyl alcohol at a rate of 35 g per bag. The above-described bag is heat-sealed to obtain an agricultural chemicals formulation.

COMPARISON EXAMPLE 4

An agricultural chemicals composition is obtained by preparing a liquid first by dissolving 3 parts of cyhalofop-butyl into 20 parts of adipic acid diisodecylester, and mixing this solution with 4.2 parts of caffenstrol, 9 parts of daimuron, 1 part of bensulfuron-methyl, 5 parts of polyoxyethylen styrylphenylether sulfate, and 2 parts of acetylene alcohol, and then mixing the whole of this liquid and 55.8 parts of wood piece (shorter diameter: 0.2 mm to 0 5 mm, bulk specific gravity: 0.23) so that the liquid is carried by the wood piece. The agricultural chemicals composition thus obtained is packed in a water-soluble film bag made of polyvinyl alcohol at a rate of 50 g per bag. The above-described bag is heat-sealed to obtain an agricultural chemicals formulation.

TEST EXAMPLE 1

Occurring of Sedimentation of the Agricultural Chemicals Formulation on the Point of the Scattering (Application) thereof.

The agricultural chemicals formulation of the present invention described in Examples 1 to 3 and 5, and the agricultural chemicals formulation described in Comparison Examples 1 to 4 are scattered (applied) in the center of a paddy field having 5 cm in depth and 2 m×2 m in area. Meanwhile, the agricultural chemicals formulation of the present invention in Example 4 is uniformly scattered (applied) on similar paddy field. Ten minutes after the scattering (application), existence of the granular nucleus settle down on the bottom of the scattered (applied) point is observed by the unaided eye and the result is evaluated with reference to the standard of evaluation for the sedimentation property described below. The result is shown in Table 1.

(Standard of Evaluation for the Sedimentation Property)

TABLE 1

| AGRICULTURAL CHEMICALS FORMULATIONS | EXISTENCE OF SEDIMENTATION ON THE BOTTOM OF THE SCATTERED POINT |
|---|---|
| EXAMPLE 1 | ± |
| EXAMPLE 2 | − |
| EXAMPLE 3 | − |
| EXAMPLE 4 | − |
| EXAMPLE 5 | ± |
| COMPARISON 1 | ++ |
| COMPARISON 2 | ++ |
| COMPARISON 3 | ++ |
| COMPARISON 4 | ++ |

| Mark for evaluation | Description |
|---|---|
| − | No sedimentation is observed |
| ± | A slight sedimentation is observed |
| + | About 10% of the chemicals thrown are observed to settle down |
| ++ | About 50% or more of the chemicals thrown are observed to settle down |

As shown in Table 1, the amount of the sediment on the bottom of water is small in the formulations of Examples 1 to 5, but is large in the formulations of Comparison Examples 1 to 4.

TEST EXAMPLE 2

Uniformity of the Constituents, Concentration of the Soil Surface Layer

The agricultural chemicals formulations described in Example 3, and in Comparison 3, are thrown and scattered in E point of the paddy field having 5 cm in depth and 10 m×10 m in area shown in FIG. 1. 24 hours after the scattering (application), water samples are withdrawn from points (A to I) shown in FIG. 1 and analyzed. The ratio of concentration of the agrochemically active ingredient obtained by analyzing the sample to the theoretical concentration when the agrochemically active ingredient is uniformly dispersed in the water is determined on the assumption that the above theoretical concentration would be 100%. Further, the degree of variability is calculated by dividing the standard deviation of the concentration in water in each point by the mean value.

The soil in each point in the extent of 10 cm in diameter and 5 cm in depth is withdrawn with a portion of water after 24 hours of the scattering (application) and is analyzed to obtain the ratio of concentration of the active ingredient of the agricultural chemicals obtained thus to the theoretical concentration when the agrochemically active ingredient is uniformly dispersed in the soil is determined on the assumption that the above theoretical concentration would be 100%. During the test, the water temperature is from 20° C. to 27° C., and the wind is blowing at the velocity of 3 m to 6 m from the point A to the point I. The result is shown in Table 2.

TABLE 2

|  | BENTHIOCARB | BENSULFLON-METHYL | MEFENACET |
|---|---|---|---|
| EXAMPLE 3 | | | |
| POINT A | 68/24 | 74/5 | 29/48 |
| POINT B | 70/26 | 72/12 | 40/51 |
| POINT C | 69/18 | 63/3 | 31/55 |
| POINT D | 65/26 | 64/11 | 32/38 |
| POINT E | 57/22 | 71/10 | 36/36 |
| POINT F | 57/21 | 60/7 | 40/47 |
| POINT G | 64/28 | 71/6 | 27/45 |
| POINT H | 52/20 | 66/9 | 31/36 |
| POINT I | 63/24 | 70/12 | 32/47 |
| MEAN VALUE (%) | 62.8/23.2 | 67.9/8.3 | 33.1/44.8 |
| DEGREE OF VARIABILITY (%) | 9.9/13.9 | 7.0/38.9 | 13.9/15.1 |
| COMPARISON 3 | | | |
| POINT A | 29/21 | 71/4 | 25/31 |
| POINT B | 28/15 | 63/4 | 31/30 |
| POINT C | 31/16 | 69/0 | 27/24 |
| POINT D | 36/18 | 64/7 | 31/28 |
| POINT E | 120/9863 | 91/1340 | 47/5631 |
| POINT F | 41/25 | 66/11 | 31/31 |
| POINT G | 42/28 | 63/8 | 24/34 |
| POINT H | 39/29 | 71/10 | 28/28 |
| POINT I | 31/20 | 65/9 | 29/25 |
| MEAN VALUE (%) | 44.1/1115.0 | 69.2/154.8 | 30.3/651.3 |
| DEGREE OF VARIABILITY (%) | 65.6/294.2 | 12.7/287.2 | 22.3/286.7 |

NOTE)
THE EXPRESSIONS IN THE TABLE INDICATE CONCENTRATION % IN THE WATER/CONCENTRATION % IN THE SURFACE LAYER OF THE SOIL

As shown in Table 2, the uniformity of the component of water, and the uniformity of the concentration of the component of the surface layer of the soil in Example 3 are satisfactory, but in Comparison 3, since a portion of the composition is settled down on the bottom of the water, the concentration of the active component of the surface layer of the soil at the point of the scattering (application) is extremely high, which causes fears of phytotoxicity.

The agricultural chemicals composition of the present invention has an effect that the agricultural active ingredients are uniformly spread over the whole surface of the paddy field without increase of concentration of the agrochemical ingredients at the point of the treatment (application) because floatability of the composition is excellent and the agrochemical ingredients would not be settled down on the bottom of the water.

Therefore, it can be advantageously utilized as a labor-saving agricultural chemicals composition or agricultural chemicals formulation which can be thrown from a path between paddy fields.

What is claimed is:

1. An agricultural chemicals composition, comprising a granular nucleus coated with a water-soluble polymer or a water-swellable substance to form closed air chambers within the granular nucleus, and one or more agrochemically active ingredients applied to said coated granular nucleus.

2. The agricultural chemicals composition according to claim 1, further comprising one or more surfactants.

3. The agricultural chemicals composition according to claim 1, wherein said agrochemically active ingredients comprise one or more liquid agrochemically active ingredients which are liquid at room temperature or liquid matter prepared by dissolving or dispersing solid agrochemically active ingredients which are solid at room temperature in a solvent.

4. The agricultural chemicals composition according to claim 1, wherein said granular nucleus has a shorter diameter of 0.1 mm to 10 mm and bulk specific gravity of 1 or less.

5. The agricultural chemicals composition according to claim 1, wherein said granular nucleus is vegetable matter.

6. The agricultural chemicals composition according to claim 5, wherein said granular nucleus is kenaf of the genus Confederate rose in Hollyhock family, Hibiscus cannabinus Linn/Hibiscus Sabdariffa Linn.

7. The agricultural chemicals composition according to claim 1, comprising a water-soluble polymer and wherein the viscosity of a 1% solution of said water-soluble polymer is 10 mPa s or more.

8. The agricultural chemicals composition according to claim 1, comprising a water-swellable substance which comprises bentonite.

9. The agricultural chemicals composition according to claim 1, wherein the content of the water-soluble polymer or the water-swellable substance is 0.01 parts by weight to 50 parts by weight for 100 parts by weight of the granular nucleus.

10. An agricultural chemicals formulation according to claim 1, wherein the agricultural chemicals composition is packed in a water-soluble film bag in an amount of 10 g to 100 g per said water-soluble film bag.

11. The agricultural chemical composition of claim 1, wherein the water-soluble polymer is present and comprises sodium polyacrylate, dextrin, polyvinyl alcohol, carboxymethyl cellulose, xanthan gum, gum arabic, polyvinyl pyrolidone or polyalkylene glycol.

12. The agricultural chemical composition of claim 1, wherein the agrochemically active ingredient comprises herbicide, fungicide and or plant growth regulator.

13. The agricultural chemical composition of claim 1 which is buoyant.

14. The agricultural chemical composition of claim 1, wherein the water-soluble polymer is present and is solid at room temperature and is not soluble in the one or more agriculturally active ingredients at room temperature.

15. The agricultural chemical composition of claim 1, wherein the water-swellable polymer is present and is solid at room temperature and is not soluble in the one or more agriculturally active ingredients at room temperature.

16. An agricultural chemicals composition obtained by:
impregnating a granular nucleus with a water-soluble polymer solution or dispersed liquid of a water-swellable substance to produce an impregnation treated granular nucleus;

drying said impregnation treated granular nucleus by evaporation to produce a coated granular nucleus with closed air chambers; and contacting said coated granular nucleus with closed air chambers with one or more agriculturally active ingredients.

17. A method for producing an agricultural chemicals composition, comprising:

impregnating a granular nucleus with a water-soluble polymer solution or dispersed liquid of a water-swellable substance to produce an impregnation treated granular nucleus;

drying said impregnation treated granular nucleus by evaporation to produce a coated granular nucleus with closed air chambers; and contacting said coated granular nucleus with closed air chambers with one or more agriculturally active ingredients.

18. The method for producing the agricultural chemicals composition according to claim 17, further comprising contacting said coated granular nucleus with one or more surfactants.

19. A method of scattering or applying the agricultural chemicals composition according to claim 1, comprising:
throwing the agricultural chemicals composition directly into a submerged paddy field at a rate of 20 g to 2,000 g per 10 are.

20. The method of scattering or applying the agricultural chemicals formulation according to claim 10, comprising:
throwing the agricultural chemicals formulation directly into a submerged paddy field at a rate of 2 bags to 20 bags per 10 are.

21. The agricultural chemical formulation of claim 10, wherein the water-soluble film bag is made from polyvinyl alcohol, polyoxy polyalkylene glycol, hydroxypropyl methyl cellulose, methyl cellulose, sodium carboxy methyl cellulose, sodium polyacrylate, alginic acid, gelatine, pulran, soluble starch, water dispersible paper or water soluble paper.

* * * * *